United States Patent
Wignall

[11] Patent Number: 6,026,560
[45] Date of Patent: Feb. 22, 2000

[54] HIGH PRESSURE MAGNET ASSEMBLY

[75] Inventor: Al H. Wignall, Friendswood, Tex.

[73] Assignee: Schlumberger Technology Corporation, Houston, Tex.

[21] Appl. No.: 08/881,583

[22] Filed: Jun. 24, 1997

Related U.S. Application Data

[62] Division of application No. 08/610,010, Mar. 4, 1996, Pat. No. 5,644,231.

[51] Int. Cl.$^7$ ...................................................... H01F 41/02
[52] U.S. Cl. .............................................. 29/607; 324/303
[58] Field of Search ................................ 29/607, 603.08, 29/602.1, 599; 324/303, 318, 322; 335/299, 296

[56] References Cited

U.S. PATENT DOCUMENTS

| | | | |
|---|---|---|---|
| 4,933,638 | 6/1990 | Kenyon et al. | 324/303 |
| 5,023,551 | 6/1991 | Kleinberg et al. | 324/303 |
| 5,046,154 | 9/1991 | MacManus | 29/607 |
| 5,055,787 | 10/1991 | Kleinberg et al. | 324/303 |
| 5,055,788 | 10/1991 | Kleinberg et al. | 324/303 |
| 5,153,514 | 10/1992 | Griffin et al. | 324/303 |
| 5,291,137 | 3/1994 | Freedman | 324/303 |
| 5,588,201 | 12/1996 | Alber et al. | 29/602.1 |
| 5,644,231 | 7/1997 | Wignall | 324/303 |
| 5,646,528 | 7/1997 | Hanley | 324/303 |

*Primary Examiner*—Louis M. Arana
*Attorney, Agent, or Firm*—John Ryberg; Brigitte L. Jeffery

[57] ABSTRACT

The present invention provides a magnet assembly capable of operating in high temperature and pressure environments without delaminating. A low viscosity resin having a low glass transition temperature can be used to assure that the magnets are completely impregnated with resin. The magnets are then assembled with the other components into a magnet assembly. Thereafter, the entire magnet assembly is placed in a metal housing and potted under temperature and pressure to eliminate voids or air spaces between assembly components in order to assure a void-free assembly.

4 Claims, 3 Drawing Sheets

HIGH PRESSURE MAGNET ASSEMBLY

RELATED APPLICATIONS

This is a Division of application Ser. No. 08/610,010 filed Mar. 4, 1996, now U.S. Pat. No. 5,644,231.

FIELD OF THE INVENTION

This invention is related to a magnet for use in a borehole and a method for manufacturing such magnet.

BACKGROUND OF THE INVENTION

When logging an earth formation, there are applications that require accurately measuring very small electromagnetic signals and phenomena. These measurements also require sensitive equipment. One such apparatus (tool) which has had practical success is a logging device which measures nuclear magnetic resonance ("NMR") properties of earth formations. Measurements of NMR characteristics of rock samples can be made in a laboratory with reasonable accuracy, but making comparable measurements in an earth borehole is rendered more difficult by the hostile borehole environments where temperatures may reach several hundred degrees Fahrenheit, pressures may reach thousands of p.s.i. and all of the equipment must be packed within a cylindrical volume of only several inches in diameter. A fundamental description of a well logging tool for measuring NMR characteristics is set forth in U.S. Pat. No. 4,933,638, assigned to the same assignee as the present application. Reference can also be made to U.S. Pat. Nos. 4,933,638 and 5,153,514 for descriptions of the conventional NMR logging approaches.

The NMR tool produces a static and substantially homogeneous magnetic field that is directed into an earth formation. By configuring and then directing the combined magnetic fields of a configuration of magnets in the NMR tool into the formation, a spatial field gradient substantially vanishes, thereby ensuring that the magnetic field is highly homogeneous throughout that region of the formation. The homogeneous magnetic field is several times stronger than the earth's magnetic field, which is thus imposed or focused on a volume of the formation in situ.

As stated, during this logging procedure, a static magnetic field is imposed on the formation. It has been recognized that particles of an earth formation such as atomic nuclei, protons or electrons have magnetic spins that tend to align with a static magnetic field $B_0$. In NMR operations, if a pulse of alternating current having a frequency f is passed through a transmitter coil, thereby producing an oscillating polarizing field $B_1$ perpendicular to the static field $B_0$, a population of protons in the formation would be tipped away from the static field direction. At the end of the pulse, when $B_1$ is removed, the protons precess about the $B_0$ vector. After a characteristic time called the longitudinal or spin-lattice relaxation time $T_1$, the protons will have relaxed to thermal equilibrium, wherein a percentage of protons are aligned in the direction of $B_0$. Formation characteristics are measured and determined from the precess of the formation particles.

The basic NMR logging apparatus used in the context of the present invention is described in U.S. Pat. No. 5,153,514 which is incorporated by reference herein and is summarized in conjunction with FIGS. 1–3. In FIG. 1, a borehole 10 is shown adjacent to formations 11 the characteristics of which are to be determined. Within borehole 10 is a logging tool 13 in accordance with the referenced U.S. Pat. No. 5,153,514 which is connected via a wireline 8 to surface equipment 7. Tool 13 has a face 14 shaped to intimately contact the borehole wall, with minimal gaps or stand-off, and a retractable arm 15 which can be activated to press the body of the tool 13 against the wall's surface. A mudcake 16 is shown on the borehole wall. Although the tool 13 is shown as a single body, the tool may alternately comprise separate components such as a cartridge, sonde or skid, and the tool may be combinable with other logging tools. Also, while a wireline is illustrated, alternative forms of physical support and communicating link can be used, for example in a measurement while drilling system. The tool 13 includes a magnet array 17 and an antenna 18 positioned between the array 17 and the wall engaging face 14. Magnet array 17 produces a static magnetic field $B_0$ in regions surrounding the tool 13. The antenna 18 produces, at selected times, an oscillating magnetic field $B_1$ which is focused into formation 12, and is superposed on the static field $B_0$ within those parts of the formation opposite the face 14. The "volume of investigation" of the tool shown in dotted lines in FIG. 1, is a vertically elongated region directly in front of tool face 14 in which the magnetic field produced by the magnet array 17 is substantially homogeneous and the spatial gradient thereof is approximately zero. The tool 13 makes a measurement by magnetically tipping the nuclear spins of particles in formation 12 with a pulse of oscillating field $B_1$, and then detecting the precession of the tipped particles in the static, homogeneous field $B_0$ within the volume of investigation over a period of time.

FIG. 2 shows a magnet array 17 disclosed in the apparatus of the above-referenced patent. The magnet array includes three permanent magnets 24, 25 and 26 which are mounted parallel to each other within a metal alloy body 27. The body 27 is a material having low magnetic permeability, so as to not interfere with the static magnetic field. Magnets 24, 25 and 26 are elongated in the longitudinal direction of the borehole. The magnetic poles of each magnet are not on the smallest faces of the slab, commonly viewed as the ends of a bar magnet; instead, the poles appear on the two opposing edges of the slab magnet and point to the left and right respectively. Therefore, within the formation 12, the magnetic field $B_0$ surrounding the magnets remains fairly constant along the longitudinal direction of the borehole axis. In the illustration of FIG. 2, magnets 24 and 26 are symmetrically mounted in the two sides of the body 27 with the north poles facing the same directions. Magnet 25 is positioned parallel to and between the other two magnets, but with its north poles facing oppositely from magnets 24 and 26. Magnet 25 is also shifted slightly away from face 14, relative to magnets 24 and 26. The north poles of magnets 24 and 26 point in the direction of the face 14 of the tool, while the north pole of magnet 25 is pointed away from the face 14. The central magnet may alternatively be reversed or omitted.

The cavity 28 is adapted for receiving an RF antenna 18 that is shown in FIG. 3. The antenna is positioned outside of the metal body 27 (FIG. 2) of the tool, and is thereby shielded from electromagnetic communication with regions of the borehole which lie behind the body 27, or regions of the other formations in directions intercepted by the body 27. Antenna 18 is thus responsive only to magnetic fields originating in front of the wall engaging face 14, e.g. fields originating in the formation 12 or in the mudcake or mud which contacts face 14 in the vicinity of the antenna 18. In a disclosed embodiment of the referenced patent, the body 27 is made of metal alloy sheathing, rigidly attached to interior metal bracing, which envelops most components of the tool other than the antenna 18, including the circuitry, the magnet array 17, and the hydraulics system of the arm 15. The patent points out that the body 27 can alternatively be constructed of other materials, so long as the overall structure is sufficiently strong and the magnetic field of the magnet array 17 can penetrate the body and enter the adjoining formation 12.

In the referenced patent, antenna 18 is used both as an RF transmitter to produce an oscillating magnetic field in formation 12 and as a receiving antenna to detect coherent magnetic signals emanating from precessing protons immediately after the oscillating field is terminated. The antenna serves effectively as a current loop which produces an oscillating field $B_1$ within the volume of investigation that is perpendicular to $B_0$.

Descriptions of the construction and functioning of the antenna are found in several U.S. Pat. Nos. (5,055,788 and 5,055,787) also assigned to the assignee of the present invention. Referring to FIG. 3, the antenna 18 comprises a highly conductive semi-cylindrical cavity or trough 29, end plates 30 and 31 and center conductor or probe 32 which extends from one end plate 30 to the other end plate 31, parallel to and centered in the semi-cylindrical trough 29. The trough 29, end plates 30 and 31 and antenna probe element 32 are indicated as preferably being of heavy gauge copper which has very low electrical resistance. Antenna probe element 32 is insulated from end plate 30 by a non-conducting bushing 33 and is connected to a conductor 34 on the other side of end plate 30. Probe 32 is attached at its other end to the other end plate 31 so that current passes freely between trough 29 and probe 32 via end plate 31. Conductor 34 is shown in FIG. 3 schematically as being connected to circuitry including an amplifier 35 and a detector 36. All connections in antenna 18 are stated to be brazed or silver soldered to ensure suitably low resistive loss. As described in the referenced patent, RF antenna 18 can be driven by amplifier 35 during specified periods of time (the signal being applied at conductor 34 with respect to the antenna body), during which it serves as an RF antenna transmitter. Alternatively, at other specified times, antenna 18 is electrically connected to detector 36, during which time it serves as an RF receiving antenna. In some modes of operation, antenna 18 may be called upon to alternatively function as transmitter or receiver in very rapid succession. The space between trough 29 and antenna element 32 is preferably filled with a nonconductive material 37 having high magnetic permeability. In order to increase the antenna sensitivity ferrite materials are preferably used. Several tuning capacitors 38 are connected between the base of antenna element 32 and the trough 29, with the capacitance thereof being chosen to produce an LC circuit, with the resonant frequency being the Larmor frequency $\omega L = \gamma B_0$.

The radio frequency antenna of the described NMR logging device must operate with very high sensitivity to the received signal. The antenna is required to sense magnetic fields at a frequency on the order of 1 MHz and a magnitude of about $10^{-12}$ Tesla. The resultant voltage induced on the antenna is of the order of $10^{-8}$ volts. This tiny voltage must be sensed within about $10^{-4}$ seconds of the cessation of the driving signal on the antenna which will typically have an amplitude of hundreds of volts. When in use as a transmitter, the antenna should produce the largest possible field for a given amount of input power. All of these difficult requirements necessitate use of a high performance antenna. As previously described, a high magnetic permeability non-metallic insulating material such as ferrite is loaded in the antenna in order to increase antenna sensitivity. However, Applicant has found that the effectiveness of the ferrite is greatly reduced by the strong static magnetic field, which can saturate the ferrite and reduce its intrinsic permeability.

To address this issue, an antenna housing or shell of high magnetic permeability material is utilized. This material effectively provides a shunt path for static magnetic field in the region of the antenna that would otherwise have deleterious effect on the ferrite and on antenna operation. The high magnetic permeability material used to form the antenna shell can be for example a mild steel. The antenna shell provides foundation support for the conductor metal of the antenna body and serves as a low magnetic reluctance path that effectively shunts magnetic fields that could otherwise saturate the ferrite loaded antenna.

The relative dimensions of antenna 18 should be selected to maximize the antenna efficiency. The slot element radius R should be as large as practical, and the spacing R-r should be maximized subject to the condition that r must not be so small as to increase the antenna impedance excessively. It has been found that for a 12 inch trough antenna without ferrite filling, R=0.75 inch and r=0.2 inch produces optimum efficiency. A ferrite filled trough antenna having dimensions R=0.75 inch and r=0.3 inch has been found to be optimum. The length L of the antenna may be the same as the length of the magnet array 17, which is 12 inches in the preferred embodiment, but antenna 18 is preferably about the same length as the resonance region produced by the magnet array 17 in the formation, which is approximately 4 to 8 inches long.

Antenna 18 is used both as an RF transmitter to produce a polarizing magnetic field in formation 12 and as a receiving antenna to detect coherent magnetic signals emanating from precessing protons immediately after the polarizing field is terminated. Antenna 18 should be constructed of one or more current carrying loops which are highly efficient in generating magnetic fields in the formation. It is preferably made of a current loop which produces an oscillating field $B_1$ within the volume of investigation which is perpendicular to $B_0$. Other current loop orientations may be useful in other embodiments of the invention having a static field $B_0$ differing from that of the preferred magnet array 17.

As previously stated, the antenna 18 is attached to body 27 and fitted within the slot 28. Its efficiency can be ideally maximized when the current density within the slot 28 is made uniform. In practice, optimum antenna efficiency is difficult to achieve because of various electromagnetic parasitic effects like the "skin effect", the mutual inductive effects between distinct current loops, and electrical effects within individual conductors.

RF antennas used in magnetic resonance applications mainly are comprised of ferrite and copper materials. Previous antenna designs involved bonding the various copper and ferrite components with epoxy. When this type of assembly was exposed to high temperature and pressure environments the assembly would delaminate. Void spaces would be found in the bond areas of the assembly. The same result occurred when the assembly was encapsulated with resin and cured under pressure. Absorption of oil was found to be a problem in the ferrites. Oil migrated under pressure into the ferrites and when the pressure was released the antenna assembly would delaminate. Typically other antennas have been fabricated by bonding with epoxy or rubber overmolding. The antennas would not withstand the environmental effects down hole because fluids or gas could migrate into the assembly during exposure to high temperature and pressure. Once gas or fluid pressure builds up in the void spaces it cannot be released quickly enough as the external pressure is relieved and the antenna component destroys itself. Still other antennas were assembled by gluing the parts together. Some parts have dissimilar thermal expansions, which cause the bonds to break under high temperatures. There is a need for an antenna assembly that is able to operate in high temperature and pressure environments without delaminating.

SUMMARY OF THE INVENTION

The present invention provides a magnet assembly capable of operating in high temperature and pressure environments without delaminating. A low viscosity resin having a low glass transition temperature can be used to assure that the magnets are completely impregnated with resin. The magnets are then assembled with the other components into a magnet assembly. Thereafter, the entire magnet assembly is placed in a metal housing and potted under temperature and pressure to eliminate voids or air spaces between assembly components in order to assure a void-free assembly.

DETAILED DESCRIPTION OF THE INVENTION

Figure 1:
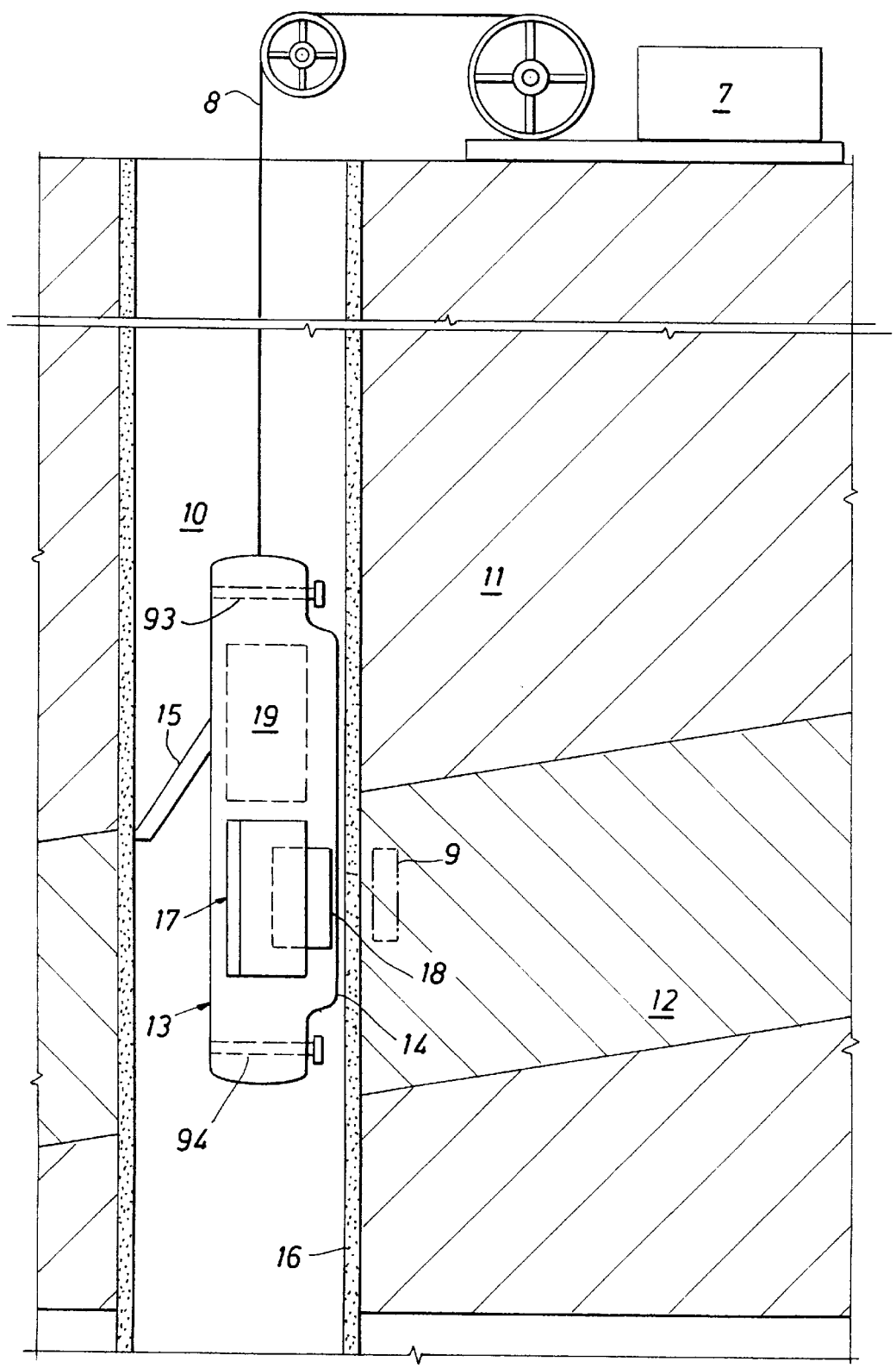
FIG. 1 is a side view of an NMR logging tool positioned in a borehole for making measurements of surrounding formations as used in accordance with the present invention.
Figure 2:
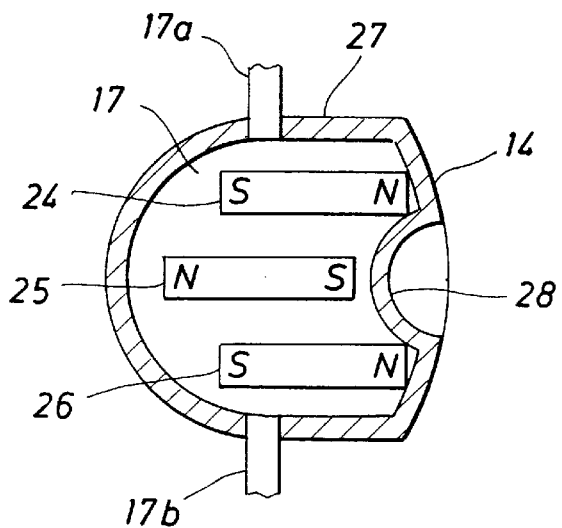
FIG. 2 is a diagram of a cross-section view of a magnet assembly that can be used in the NMR logging tool.
Figure 4:
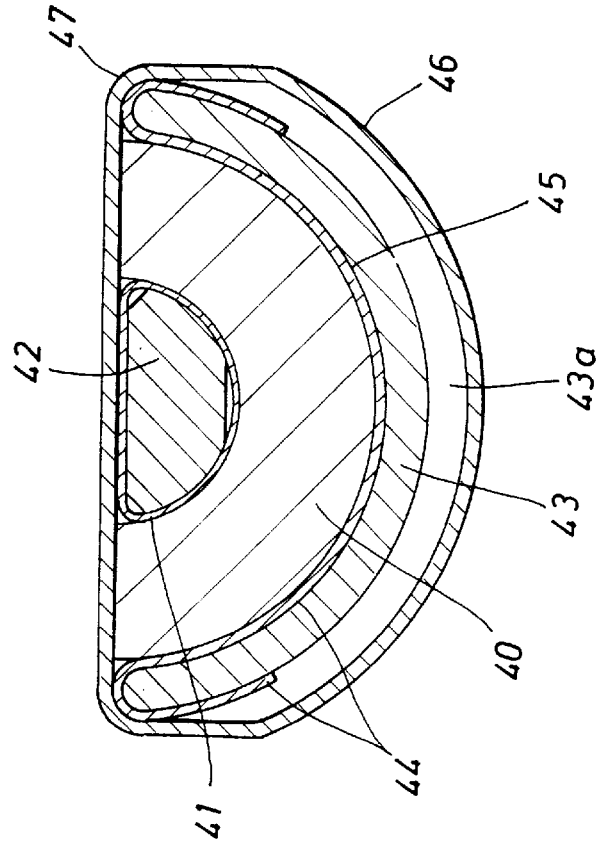
FIG. 4 is a diagram of a cross-section view of an antenna forming the present invention.

Referring to the FIG. 4 and as previously described, the antenna is comprised of a ferrite material 40 such as iron oxide which provides an inductive load to the antenna. During the manufacturing of the antenna, the ferrite material is impregnated at approximately 300° F. temperature and 10,000 psi pressure with an epoxy resin that is flexible and has a low (below 250° F.) transition glass temperature. This epoxy resin fills any void spaces in the ferrite material to prevent delamination of the material when exposed to high borehole temperatures and pressures during the well logging procedure. The ferrite material has a cylindrical shape with a trough in its center. A probe which is the current carrying part of the antenna rests in the trough. The probe is comprised of an electrical conductor material 41 enclosing an epoxy filler material 42. This epoxy filler center 42 serves as a gap filler. The epoxy filler 42 is also impregnated at approximately 300° F. and 10,000 psi pressure with a low viscosity resin. Surrounding the epoxy filler center conductor is a copper sheet outer conductor 41. This conductor is the current carrying component of the antenna. A cylindrically shaped magnetic shield 43 surrounds the ferrite material 40 and shields it from the magnetic field generated by the magnet array 24, 25 and 26 shown in FIG. 2. The magnetic shield is partially surrounded by a copper sheet 44. This copper sheet 44 is connected to copper sheet 41 via end plate 31 and is also part of the current carrying means of the antenna. A fiberglass reinforced composite material 43a surrounds the magnetic shield and copper sheet and provides a fit for the antenna into the logging tool. Between the magnetic shield and the copper sheet 44 is an insulation material 45 (usually rubber) that dampens acoustic vibration of the antenna conductor. The entire assembly 40, 41, 42, 43, 43a, 44, and 45 is assembled as shown and wrapped in fiberglass 46 under high pressure of approximately 10,000 p.s.i. This fiberglass wrap acts as a band and forces the components together. Since the fiberglass has a low coefficient of expansion in the direction of the wrap, the assembly is held tightly together. Other fiber reinforcement materials could also be used provided they have expansion characteristics similar to the other components of the particular assembly. Regardless of the material, this wrap technique provides a more reliable means to keep the antenna assembly intact than by the previous methods of gluing, bonding or potting the components together. The fiberglass wrap, by holding the assembly together, also keeps the antenna from ringing caused by vibrations.

Referring to FIG. 4, one embodiment of the antenna assembly has an outer radius (exterior surface) of the fiber glass wrap 46 of approximately 2.49 centimeters and an inner radius exterior surface of the magnetic shield 43 of approximately 2.1 centimeters. The outer radius includes the fiberglass wrap. The individual radii of the ferrite material 40 and the epoxy filler material are approximately 1.905 centimeters and 1.27 centimeters respectively. The antenna also has two widths. The outer width including the fiberglass wrap is approximately 4.92 centimeters and the inner width is approximately 4.24 centimeters. The fiberglass wrap has a top portion 47 that has a thickness of approximately 0.10 centimeters. The majority of the fiberglass wrap (the sides and curved portions) has a thickness of approximately 0.279 centimeters.

Figure 3:
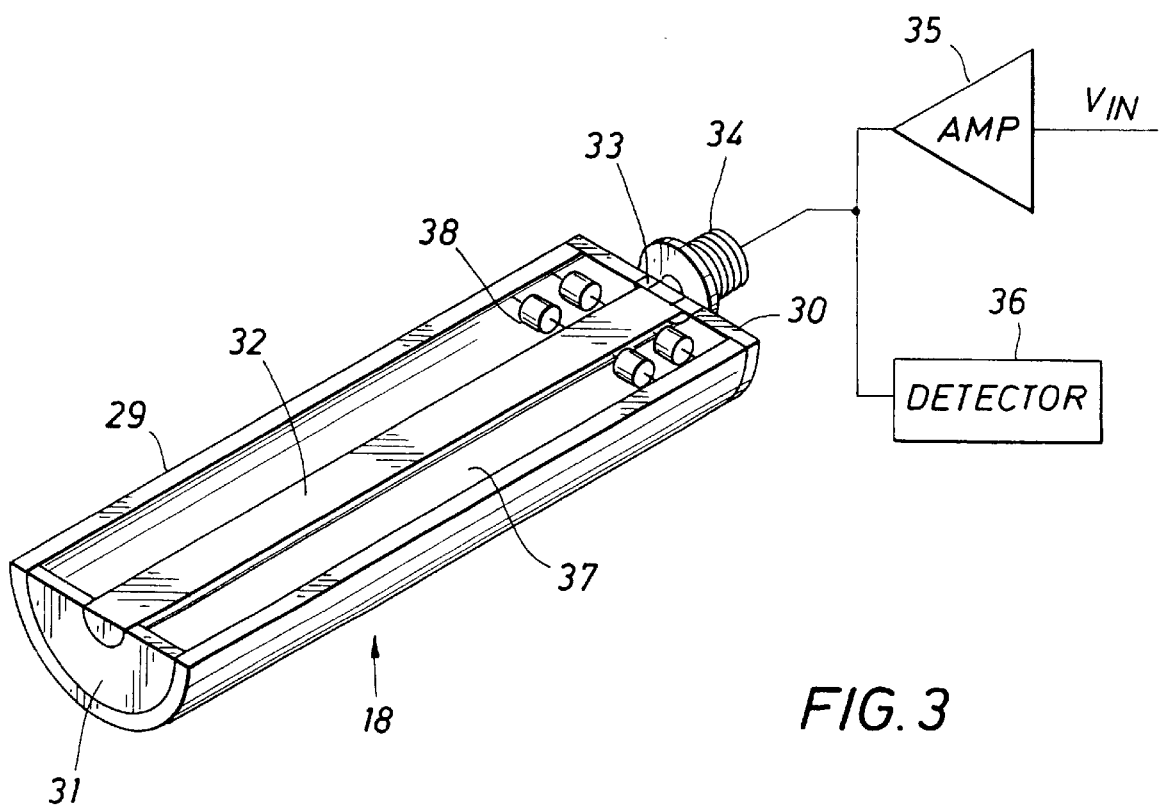
FIG. 3 is a perspective view, partially in block form of a prior art antenna used in the NMR tool.

In the process of manufacturing and assembling the antenna, the ferrite and filler materials 40 and 42 are potted separately under temperature and pressure and these conditions are maintained until the resin is cured. The ferrite material 40 and the epoxy filler material 42 are first impregnated with a low viscosity resin such as polyester at 300° F. and 10,000 p.s.i. The epoxy filler material is then wrapped with a sheet of copper 41. The ferrite material 40 is covered with a magnetic shield 43 of iron material. However, before covering the ferrite material, the magnetic shield 43 is partially covered with a sheet of copper 44. Copper sheets 41 and 44 are connected by end plate 31 (see FIG. 3) and comprise the current carrying conductor of the antenna. As previously stated, the current produces an RF field that causes the hydrogen protons in the formation to align. In addition, between the copper sheet 44 and the magnetic shield 43 is a thin sheet of rubber 45 that serves as a vibration damper. The antenna assembly is then loosely assembled and wrapped with a fiberglass material 46 under approximately 10,000 p.s.i. of pressure to reinforce the assembly. The entire assembly is then potted under temperature and pressure which frees the assembly of any remaining void spaces.

At this point the remainder of the antenna construction is usually similar to that of the previously mentioned patents. Typically, other antennas have been fabricated by bonding with epoxy or rubber overmolding. The conventional antennas would not be able to withstand the environmental effects down hole because fluids and gases could migrate into the assembly thereby allowing exposure to high temperature and pressure.

Figure 5:
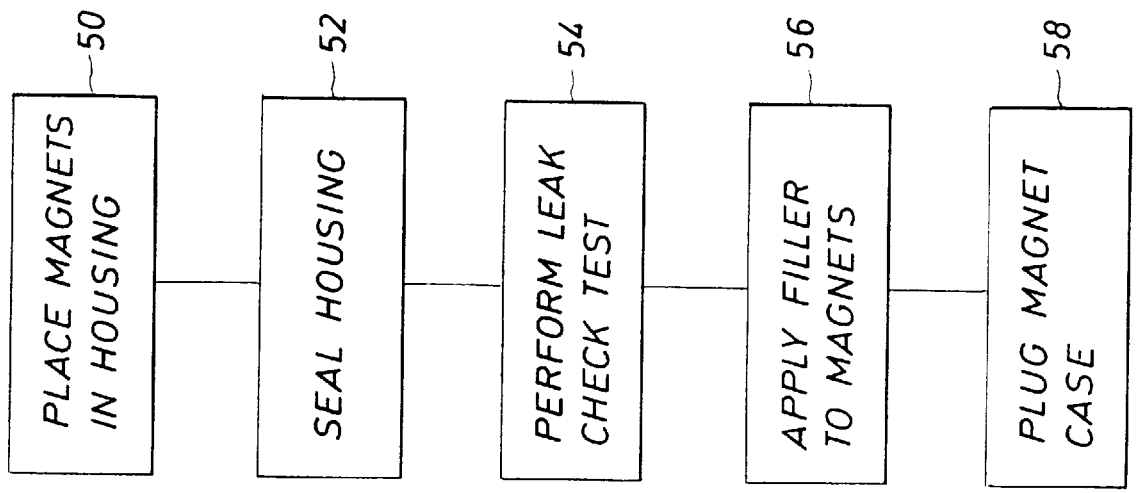
FIG. 5 is a flow chart of the process for manufacturing the high pressure magnet assembly of the subject invention.

The construction of the magnet array components 17 of the previously described NMR logging apparatus (see FIG. 2) can also be improved in a manner similar to that of the present invention to protect the magnet material from being exposed to the downhole environment and to withstand high temperatures and pressures. Referring to FIG. 5, the magnets can be hermetically sealed in a metal housing and filled with a solid material to withstand temperature, pressure and the corrosive effects of drilling fluids (steps 50 and 52). The process uses conventional tungsten inert gas welding techniques. The conventional welding is possible by shunting the magnetic field away from the weld area and to a low flux density. After a magnet case has been welded it can be checked by a helium leak test (step 54). The magnets are vacuum impregnated with an epoxy filler through leak check ports 17a and 17b (step 56). The epoxy can be cured under high pressure of approximately 20,000 psi and a temperature of approximately 370° F. while in a pressure balanced condition. The case is then plugged (step 58). Since all of the material inside the case is a close thermal match with the case, the magnet acts as an incompressible solid and is able to withstand the borehole conditions.

The invention has been described with reference to a particular preferred embodiment, but variations within the spirit and scope of the present invention will occur to those skilled in the art. Those skilled in the art will recognize that numerous variations and modifications may be made without departing from the scope of the present invention. Accordingly, it should be clearly understood that the forms of the invention described hereinabove are exemplary, and are not intended as limitations on the scope of the invention, which should be defined only by the claims, appended hereto.

We claim:

1. A method of manufacturing and assembling a magnet comprising the steps of:

a) assembling magnets in the desired configuration;

b) placing said assembled magnets in a metal alloy housing, said housing being made of a material having low magnetic permeability, said housing having a leak check port;

c) hermetically sealing said housing;

d) performing a helium leak check test on said housing;

e) vacuum impregnating said magnets with an epoxy filler through said leak check port, said housing being in a pressure balanced condition;

f) curing said epoxy filler under high temperature and pressure while maintaining said pressure balanced condition; and g) plugging said leak check port.

2. The method of claim 1 wherein said sealing step is performed by tungsten inert gas welding.

3. The method of claim 1 wherein said leak check test is performed through said leak check port.

4. The method of claim 1 wherein said curing step is performed at a pressure of about 20,000 psi and at a temperature of about 370° F.

* * * * *